United States Patent [19]

Kunig

[11] Patent Number: 4,622,980

[45] Date of Patent: Nov. 18, 1986

[54] METHOD AND APPARATUS FOR DETERMINING OF STRESS CONDITION OF A SUBJECT

[75] Inventor: Horst E. Kunig, Box 577, R.D. 1, Saltsburg, Pa. 15681

[73] Assignees: Horst E. Kunig; John N. Robinson, both of Pittsburgh, Pa.

[21] Appl. No.: 667,129

[22] Filed: Nov. 1, 1984

[51] Int. Cl.[4] .............................................. A61B 5/04
[52] U.S. Cl. .................................... 128/704; 128/707
[58] Field of Search ............... 128/696, 700, 702, 704, 128/707–708, 716, 903–904

[56] References Cited

U.S. PATENT DOCUMENTS

| 3,554,187 | 1/1971 | Glassner et al. | 128/703 |
| 3,572,321 | 3/1971 | Bloomfield | 128/704 |
| 3,832,994 | 9/1974 | Bicher et al. | 128/702 |
| 4,319,241 | 3/1982 | Mount | 128/903 |
| 4,409,985 | 10/1983 | Sidorenko et al. | 128/707 |
| 4,475,558 | 10/1984 | Brock | 128/716 |

FOREIGN PATENT DOCUMENTS

| 520975 | 10/1976 | U.S.S.R. | 128/704 |
| 665888 | 6/1979 | U.S.S.R. | 128/707 |

Primary Examiner—William E. Kamm
Assistant Examiner—Mitchell J. Shein
Attorney, Agent, or Firm—Harry B. Keck

[57] ABSTRACT

A method and apparatus for establishing a stress index S of a subject by determining from the EKG of the subject the peak valve of the R-wave and the T-wave; determining the ratio of the R-peak to the T-peak as an initial stress value Z; determining the corresponding stress value Z after the subject experiences stress or relief of stress and establishing the stress index S as the ratio of the Z values (after/before). A stress meter is proposed to provide visual or other indications of the instantaneous stress index. Methods of exercising subjects or treating subjects in accordance with stress index values are disclosed.

22 Claims, 15 Drawing Figures

FIG. 11 Stress Index During Cardiopulmonary Vital Capacity Measurement

FIG. 12 Stress Index During Oxygen Inhalation

FIG. 13 Stress Index During Medication Therapy

METHOD AND APPARATUS FOR DETERMINING OF STRESS CONDITION OF A SUBJECT

BACKGROUND OF THE INVENTION

1. Field of the Invention

This invention concerns a method and apparatus for measuring the instantaneous stress condition of a subject while the subject is experiencing either a system stress, such as physical exercise, or relief of a system stress such as response to inhalation and exhalation of air, or response to oxygen-enriched air ventilation, or response to cardiac stimulants.

2. Description of the Prior Art

In the training of athletes, a program of severe physical exercise is frequently prescribed to extend the athlete's performance. For example, in conditioning an athletic team, a common program of calisthenics is provided for all members of the team. Some particularly capable team members are not sufficiently stressed by the common program whereas other less capable team members may be overstressed by the common program to the degree of life endangering stress exposures. The more capable athlete is not experiencing sufficient exercise whereas the less capable athlete may be dangerously overstressed. It is desirable to develop a technique for stressing each individual athlete to an optimum level whereby each individual athlete can benefit from the exercise program and extend his performance capability without endangering overall physical condition or risking burnout. Currently the three methods employed to obtain this information are (1) maximum oxygen comsumption; (2) lactic acid measurement; (3) heart rate measurement.

Maximum Oxygen Consumption

The maximum oxygen consumption ($VO_{2\ max}$) is employed to determine the fitness level of a subject. High values are desirable for athletes who have $VO_{2\ max}$ values of 70-75 ml/kg/min. Elaborate equipment is required for quantitative measurement of the $VO_{2\ max}$ by analysis of the expired air from the subject while the subject is performing maximum work effort—for example on a treadmill or a bicycle or an ergometer—while the subject has a breathing hose in his mouth which is connected to a stationary gas analyzer. From analysis of the expired gases it is also possible to determine the subject's aerobic/anaerobic threshold. While this technique can be used to determine the level of fitness of a subject, little information can be deduced as to a practical daily work-out regimen for a training athlete or for a health-conscious subject engaged in recreational exercises.

Lactic Acid Measurements

Appropriate exercise levels for improving general fitness by elevating the $VO_{2\ max}$ are difficult to design. A useful, but impractical, time consuming, expensive, body-invasive and non-instantaneous technique is the measure of accumulated lactic acid in blood samples which are drawn from the subject's ear lobe following exercise. The more strenuous the exercise, the larger the lactic acid concentration. A lactic acid accumulation of 4 millimoles per liter indicates a switch of metabolism from aerobic to anaerobic which is the generally accepted exercise level for endurance training of an athlete. However the time required to obtain the lactic acid measurement is substantial and the necessary information is not available until long after the subject's workout is completed. The athlete's trainer thereafter employs the information obtained from the previous workout and analysis to design the succeeding work-out and conducts further blood tests. This technique also requires skilled analytical personnel and special biochemical laboratory equipment.

Heart Rate Measurements

A practical, but empirical, method is the measurement of heart rate. There are recommendations that the subject heart rate should increase to a level of 60 to 80% of the maximum heart rate—which is statistically determined for each subject's age and general condition. This technique provides instantaneous information, but because it is based upon statistical features rather than characteristics unique to the subject, the information is of limited value and may be truly dangerous in specific cases because of idiosyncrasies of the individual subject which are distinct from the statistical values. It is desirable to develop simple instrumentation.

Other Techniques

In the treatment of medical patients requiring oxygen ventilation, the concentration and flow rate of oxygen-enriched air being inhaled is derived by taking arterial and venous blood samples and measuring blood gases such as oxygen ($pO_2$) and carbon dioxide ($pCo_2$). Since this technique is impractical, invasive and painful, its use is customarily restricted to patients in intensive care units.

Another method is the transcutaneous method where an oxygen-sensing device is placed directly on the skin of a patient. Since the oxygen being sensed must diffuse through the skin layers which are different for different subjects, this method yields no absolute results as far as $pO_2$ is concerned but only indicates the trend as a result of a medical intervention. Further it is well known that too high a concentration of oxygen inhaled at too large concentrations causes toxic effects and may in extreme cases cause death. It is therefore desirable to develop a technique which would indicate in a non-invasive, simple, instantaneous, continuous and practical manner whether oxygen inhalation relieves the system stress as it should in a beneficial oxygen inhalation, or conversely, contributes to the system stress in the case of a non-beneficial, toxic inhalation.

In order to assess general cardiopulmonary health or fitness a subject may be asked to undergo a stress test on a treadmill where the maximum oxygen consumption is determined. This procedure is elaborate, not free of health risks and must be performed by skilled personnel.

It is therefore desirable to develop a technique whereby the changes of the EKG pattern created by deep inhalation and exhalation of air are used to determine the cardiopulmonary condition, recognizing the fact that deep inhalation of air oxygenates the body corresponding to a relief of stress and exhalation of air deprives the body of oxygen corresponding to the application of stress.

It is further desirable to develop a simple stress sensing device for instant assessment of cardiopulmonary condition, for continuously monitoring and maintaining the cardiopulmonary status of a subject, to monitor the efficacy of cardiopulmonary rehabilitation and health maintenance programs.

In order to assess the efficacy and safety of cardiac stimulants, especially medication indicated in case of cardiac abnormalities, elaborate measurements are necessary such as cardiac output measurements, systolic time interval measurements, ST depression, etc., which are frequently not sensitive to incremental changes of heart conditions. It is therefore desirable to develop a simple, instantaneous and continuous measuring technique requiring no skilled personnel to sense relief of stress caused by taking a cardiac stimulant in order to assure efficacy of the stimulant or to sense the increase of stress which indicates renewed application of medication, or need for activating a cardiac procedure, or other responsive treatment.

It has been discovered that the electrocardiographic pattern changes with application of stress or relief of stress and that the ratio of the R wave amplitude to the T wave amplitude, determined after application of stress, is greater than the ratio of the R wave amplitude to the T wave amplitude before application of stress. Therefore the quotient of the two ratios, herein called stress index S, is greater than 1 when the subject is stressed. It has also been discovered that in the case of stress relief the stress index S is less than 1. The instantaneous value of the ratio of R peak T peak is called herein the Z-Value.

It is the object of this invention to provide simple, inexpensive, non-invasive, instantaneous measuring means and instrumentation, herein called a stress meter to be used by unskilled personnel to sense application of stress or relief of stress in a subject for the purpose of determining optimal stress level for exercise, for general quick assessment of cardiopulmonary status, for monitoring the efficacy and safety of oxygen inhalation therapies and rehabilitation therapies, for assessing success of rehabilitation therapies and for monitoring efficacy of cardiac stimulant therapies. It is understood that these applications are only examples of a large category of the objects of the invention.

It is well known to record electrocardiograph phenomena of humans but the application of electrocardiograph data to the maximum stress threshold appears to be unexplored. Numerous devices for obtaining electrocardiograph data and for selecting appropriate portions of electrocardiograph data are known. See, for example, BLOOMFIELD et al; U.S. Pat. No. 3,572,321; ZENEVICH et al, U.S. Pat. No. 3,605,727; THORNTON, U.S. Pat. No. 3,267,934; KOEBLITZ, U.S. Pat. No. 3,709,212; McINTYRE, U.S. Pat. No. 3,908,639; GLASSNER et al, U.S. Pat. No. 3,554,187; ANDERSON, U.S. Pat. No. 3,858,034; NEILSON, U.S. Pat. No. 3,940,692; MURPHY, U.S. Pat. No. 4,137,910. None of these references provides a method for determining the instantaneous stress condition of the observed subject.

BLOOMFIELD et al supra recognized a relationship between the value of the T (peak amplitude) and the value of the R (peak amplitude) and recommend that the ratio of T-peak to R-peak be determined. This ratio is the inverse of the present Z-value. According to BLOOMFIELD et al, if the ratio T-peak/R-peak is less than approximately 0.12 to 0.18 (corresponding to Z values greater than 8.3 to 5.6), then further electrocardiograph measurements are warranted. Conversely, BLOOMFIELD et al recommend that where the ratio T-peak/R-peak is greater than approximately 0.12 to 0.18 (corresponding to Z values less than 8.3 to 5.6), the subject individual does not require electrocardiograph measurements. BLOOMFIELD et al thus employ the ratio T-peak/R-peak as a screening device for abnormal heart conditions claiming validity of this procedure to be 80%. The Bloomfield et al ratio T-peak/R-peak also varies through the day and from day-to-day and depends on the body position of the subject, i.e., whether the subject stands upright or lies down or moves around, and is affected by other circumstances. Since the BLOOMFIELD et al ratio T-peak/R-peak changes for successive heartbeats as a result of normal breathing procedures of a subject, the technique is of dubious reliability or validity.

STATEMENT OF THE INVENTION

What I have discovered is that the Z-value alone is unique for each person and therefore of little diagnostic value if any. Competitive athletes have been measured whose Z-value would warrant further investigation as to possible cardiac abnormalities according to Bloomfield et al. What I also have discovered is that the Z-values change with application or relief of stress and, importantly, that these changes directly correlate quantitatively with the amount of stress applied and therefore with the stress level of the subject. Accordingly I have developed apparatus and means to measure the Z value or its appropriate sliding averages, averaged over a number of heart beats and time, in a subject firstly in a condition of rest and to identify this initial Z-value as "Z before stress application/relief of stress." Thereafter the subject is exposed to some form of stress or relief of stress. The stress may be repetitive physical exercise, treadmill exercise, calisthenics, swimming, bicycle riding, exercise machines, running, walking, etc., which causes the Z-value to increase. The relief of stress may be oxygen inhalation which causes the Z-value to decrease. The prevailing Z-value during or after termination of the stress or relief of stress at any given time is measured and identified as "Z after application of stress or relief of stress." Such Z-values may be the Z-value of one particular heart beat or appropriate averages over a number of heart beats and or time, depending on the specific measurement which is carried out. Then the ratio of "Z-after" to "Z-before" is determined and is called herein the Stress Index S.

According to the present invention I have discovered a ratio which I have called Stress Index S which can be related to the instantaneous stress condition of an observed subject. The stress index S is derived from a stress value Z which increases with application of stress and decreases with relief of stress. The stress index can be indicated as Z (after application/relief of stress) over Z (before application/relief of stress), i.e., $$S = \frac{Z(\text{After})}{Z(\text{Before})}$$

In case of stress application, Z increases. Hence the Z-values after stress application are greater than the Z values before stress application. Therefore the ratio of Z(after) over Z(before) has a value greater than 1, i.e., stress index S is greater than 1.

In case of stress relief, Z decreases. Hence the Z-values after stress relief are smaller than the Z-values before stress relief. Therefore the ratio Z(after) over Z(before) has a value less than 1, i.e., stress index S is less than 1. An indication of S=1 occurs when stress is neither applied nor relieved, i.e., the subject is at rest.

The two cases establish a cardiopulmonary stress scale where the stress index S ranges from 0 to 10. S<1 indicates stress relief and S>1 indicates stress application.

Thus the present invention is directed to an electromechanical device for indicating cardiopulmonary stress condition of a subject and includes appropriate means for developing the EKG wave of the subject including electrical sensors which are positioned on the subject in suitable locations for establishing a well defined P, R and T wave. The invention further includes appropriate means for determining and recording the ratio of the R-peak to the T-peak while the subject is at rest in order to establish a stress value $Z_{Before}$. The invention includes further means for determining and recording the ratio of the R-peak to the T-peak as the subject is subjected to stress or to relief of stress in order to establish the stress value $Z_{After}$. The invention further includes appropriate means for establishing the subject's stress index S as the ratio of $Z_{After}$ to $Z_{Before}$ and includes additional means for indicating the value of the stress index S such as a visible digital display, a permanent recorder, a visible or audible alarm, a monitor outlet and the like. Preferably the electromechanical device includes means for determining the average value of the stress value Z over a predetermined number of heartbeats or over a predetermined time interval. Preferably the device includes appropriate electronic memory circuitry for storing values of Z and S. The device may include means for developing an identifiable signal when certain pre-established values of the stress index S are exceeded in a maximum or minimum direction.

In a further refinement of the invention, the stress meter is provided with telecommunication means for delivering an electrical signal corresponding to a subject's EKG waves, particularly the R-peak and T-peak waves to a remote stress index meter for analysis. In a further refinement the stress meter may be provided with telecommunication means for delivering a signal back to the subject in a remote location.

In particular end-use applications, the stress meter index may be employed in combination with exercising machines which may be provided with regulating means to increase or decrease the resistance of the exercising machine in response to the instantaneous value of the stress index.

The following drawings and the detailed description of preferred embodiments as well as the practical examples will provide a more complete understanding of the invention and the objectives of the invention.

DESCRIPTION OF THE PREFERRED EMBODIMENTS

Figure 1:
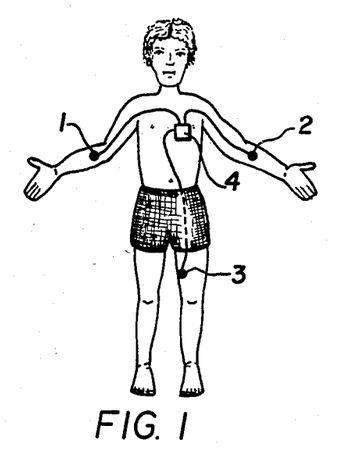
FIG. 1 is a representation of a human subject showing typical location of sensors employed in the practice of the present invention.
Figure 2:
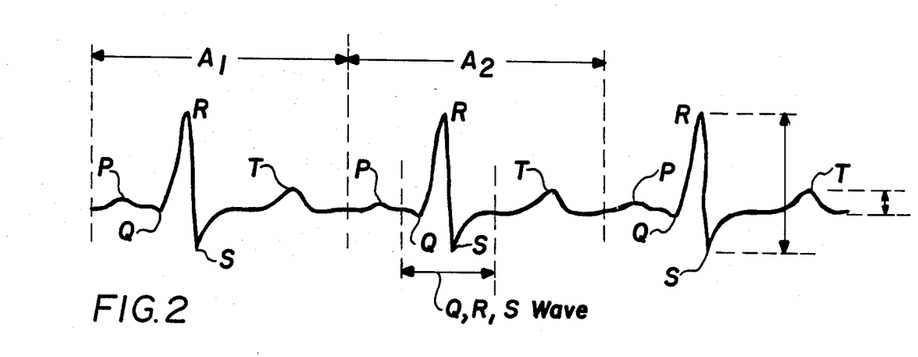
FIG. 2 is a graphical representation of a typical electrocardiograph (EKG) wave illustrating the familiar P, Q, R, S, T features.

According to the present invention, a subject under observation is provided with three electrocardiograph sensors as shown in FIG. 1 located so as to produce sharply discriminated Q-R-S waves and T waves. As an example, an electrical ground sensor 3 may be applied to the right leg; a right arm sensor 1 and left arm sensor 2 may be applied to the lower arms between the elbow and the wrist. In general, sensors located as shown in FIG. 1 will produce optimum electrocardiograph signals of the type shown in FIG. 2. As shown in FIG. 2, a typical electrocardiograph pattern includes repetitive oscillating signals A1, A2 each which of contains a P-peak, an R-peak and a T-peak along with a Q-node and an S-node. The duration of the waves A1, A2 depends upon the instantaneous pulse rate of the subject.

According to the present invention, the electrocardiograph signals from sensors 1, 2, 3 are applied to a device 4 which transmits the electrocardiographic signals by radio, by telemetry or through conductors 1a, 2a, 3a to an EKG 4A which produces instantaneous EKG patterns of the type shown in FIG. 2. The device 4 may be connected through an electrocardiograph 4A to an analytical device 4B (FIG. 3) which is called stress meter.

Figure 3:
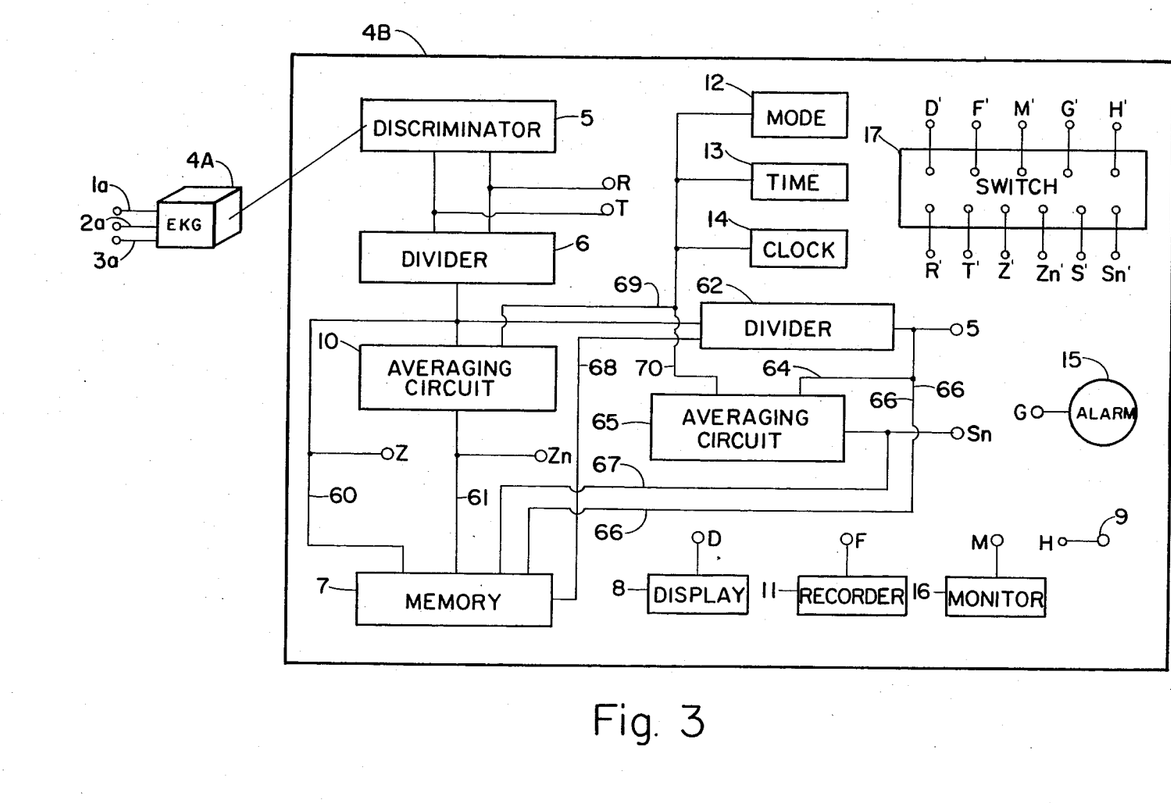
FIG. 3 is a schematic illustration of equipment for practicing the present invention.

The stress meter 4B determines the amplitude of the Q-R-S wave (called the R-wave) and the amplitude of the T wave in a discriminator 5. The ratio of the amplitude of the R-peak to the amplitude of the T-peak is determined in the divider 6 to establish an instantaneous stress value Z.

Voltages representing the instantaneous amplitude of the R-peak and the T-peak and applied to the divider 6 and to terminals identified as "R" and "T" respectively. The instantaneous stress value Z may be stored in a memory device 7 through a conductor 60 and applied to a terminal identified as "Z".

Figure 4:
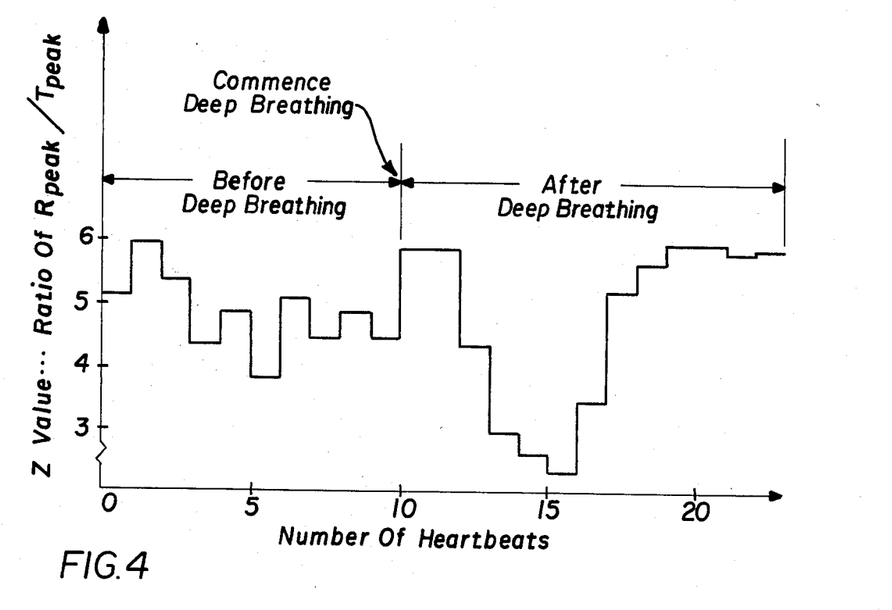
FIG. 4 is a graphical representation of the change of the stress index for successive heart beats.

The stress value Z changes from heartbeat to heartbeat with the rhythm of inhaling and exhaling air as shown, for example, in FIG. 4 wherein the results of inhalation and exhalation of air are indicated. FIG. 4 presents the measured Z-value for a normal healthy subject. Over the space of 10 heartbeats, 8.8 seconds, the patient breathed normally at rest and exhibited Z-values ranging from 3.8 to 6.0. After 10 heartbeats, the patient commenced deep inhalation of air and the Z-value reduced from 5.8 to 2.8 in the course of 7 heartbeats corresponding to the first deep inhalation. The first exhalation following the 7 heartbeats resulted in an instantaneous increase in the Z-value to levels of 5.2–6.0. FIG. 4 indicates the importance of averaging Z-values over a significant number of heartbeats and/or inhalation/exhalation cycles to observe meaningful trends. Thus it is important to derive a correct reliable value of "Z before stress is applied or relieved" as the base reference in the present diagnostic technique.

An averaging circuit 10 calculates sliding averages of the Z-value over a preselect number N of heartbeats Z(N) or a sliding average the Z-values over preselected time Z(T). The average stress value Zn from the averaging circuit 10 may be stored in the memory 7 through a conductor 61 and applied to an outlet terminal identified as "$Z_n$". The initial Z-number or Z(N) or Z(T) identified as Z (before) is stored in a memory bank 7. Continuously or intermittently after a stress is applied or relieved, instantaneous Z-values or appropriate averages in form of Z(N) or Z(T) are measured depending on the specific application, and are identified as Z(after). The Z(after) values are compared in a divider 65 with the Z(before) value, from the memory 7, to establish the stress index S at each measurement. In order to calculate the Stress Index S, the instantaneous stress value Z is applied to the divider 62 through a conductor 63. The value of Z(before) is withdrawn from the memory 7 through conductor 68 to the divider 62. The instantaneous Stress Index is delivered from the divider 62 through a conductor 64 to an averaging circuit 65. The averaging circuit 65 develops the average Stress Index which may be stored in the memory 7 through a conductor 67 and applied to an output terminal identified as "$S_n$". The stress index S for each heartbeat, or a sliding average over N heartbeats S(N) or a sliding average over a preselected time S(T) are displayed in a display device 8, having an input terminal "D" may be recorded in a memory bank 7 through conductors 66, 67 perspectively, may be delivered to an outlet jack 9 through an input terminal "H" as a control signal, or to recorder 11 having an input terminal "F".

A mode selector switch 12 permits the selection of N, the number of heartbeats over which the sliding average is to be calculated to form Z(N). A time selector switch 13 permits the selection T, of time over which Z is to be averaged to form Z(T). A clock 14 is provided to measure the time. A light or alarm 15 having a terminal "G" is provided to indicate that the reference value Z(before) stress has been established and will be stored in the memory bank 7. An appropriate control signal from the mode selector switch 12, and the time selector switch 13 and the clock 14 is delivered through a conductor 69 to the averaging circuit 10 and through a conductor 70 to the averaging circuit 65. A monitor 16 having a terminal "M" is provided to indicate when pre-established values of S are reached after stress is applied. The monitor 16 may be a light, an audible alarm, an output jack at which an electric signal develops or other useful device. A switch 17 is provided to recall and or recalculate the reference value Z(before) at any given time. The switch 17 has input terminals R', T', Z', $Z_n'$, S' and $S_n$ which are connected to the terminals R, T, Z, $Z_n$, S and $S_n$, respectively. The switch 17 has output terminals D', F', M', G' and H' which are connected to the terminals D, F, M, G and H respectively. Thus the switch 17 can display or record or monitor or follow any of the functions from the terminals R, T, Z, $Z_n$, S or $S_n$ in the display device 8, the recorder 11, the monitor 16, the output terminal 9 or the alarm 15.

Figure 5:
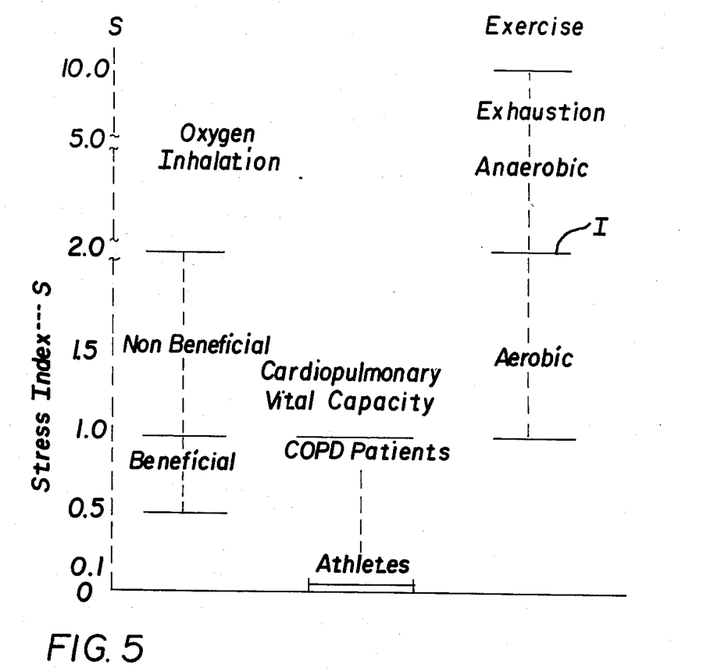
FIG. 5 is a graphical representation of the cardiopulmonary stress scale.

The utility, novelty, significance and the objects of the invention are summarized for various applications in FIG. 5 which shows the cardiopulmonary stress scale. The vertical scale of stress index S ranges from 0 to 10. If a subject is at rest, the stress index S always equals 1. The reason for S=1 at rest is that $Z_{Before}$ is derived initially and is stored in the memory 7. After that event, the stress meter compares each subsequent Z value with $Z_{Before}$. If no stress has been applied or relieved, each subsequent Z-value equals the $Z_{Before}$. Hence the ratio of $$\frac{Z \text{ value}}{Z_{Before}} = S = 1$$

After application of stress, the stress index S increases and may reach values of 10. After stress relief, the stress index decreases to values less than 1. The term cardiopulmonary vital capacity is defined as the changes of the stress index S which occur during inhalation and exhalation of air.

FIG. 5 illustrates graphically three different applications. All three of the applications commence with a base value of 1.0, reflecting the condition of the subject before stress or stress relief. When oxygen inhalation is employed, the S value should decrease below 1.0 if the therapy is beneficial. If the therapy is non-beneficial, the stress index will be greater than 1.

Where the subject exercises following the determination of the value of Z(before), initial exercise will create a stress and the stress index will rise above 1.0 to some value, different for each subject, during which the subject's condition will remain aerobic. However for each subject there is a higher level stress index indicated in FIG. 5 as level I, where the subject's metabolism converts from aerobic to anaerobic. Continued application of stress beyond the level I (FIG. 5) results in increasing anaerobic characteristics which in severe instances results in exhaustion, collapse and fatality.

1. Exercise 1.1 Running

Simultaneous measurements of stress index S and lactic acid accumulation were made for a subject performing a treadmill test. A correlation between S and lactic acid accumulation was found. The stress index value of 2 corresponds with a lactic acid accumulation of 4 milli-moles per liter thus permitting an easy identification of aerobic/anaerobic threshold as identified by a stress index of 2. A stress index above 5 typically corresponds with a state of exhaustion, as indicated in FIG. 5.

Figure 6:
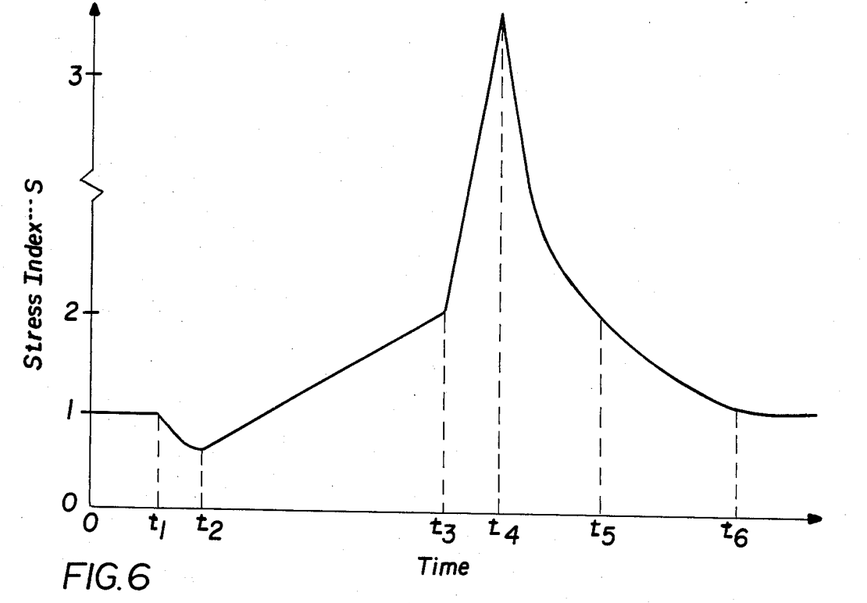
FIG. 6 is a graphical representation of the change of the stress index S during and after exercise.

As shown in FIG. 6, after a subject is connected to a stress meter and a stress reference value Z(before) equals 1 has been established, the subject begins to exercise at time $t_1$. In the initial phase of the exercise from $t_1$ to $t_2$, the stress index S decreases which corresponds to the subject's warm-up phase.

The monitor 16 detects the minimum value of S to indicate the end of the warm-up period, hence permitting the correct design and quantitative control of appropriate warm-up procedures.

Continued exercises after $t_2$ increases the stress index S to values greater than 1 which is the work-out phase. When monitor 16 indicates that the stress index value S equals 2, the subject's metabolism is changing from aerobic to anaerobic, and further work-out is not beneficial and is contra-indicated. This transition is seen in FIG. 6 at time $t_3$.

If a subject works out too little as indicated by a peak stress index S less than 1.5, little progress is made as far as improvement of athletic capabilities is concerned in that work-out. This is seen in FIG. 6 if the work-out ended prior to the time $t_3$. If a subject works out too hard in the anaerobic metabolism regimen as indicated by a stress index S greater than 2, no athletic progress is made because of burn-out. Monitor 16 is used to indicate the switch of the metabolism thus permitting the correct design and quantitative control of optimum work-out procedures. As shown in FIG. 6, the subject worked out in the aerobic metabolism regimen from $t_1$ to $t_3$.

Further increase of the work load or exercise stress causes the stress index S to increase to values of 10. The quantitative relationship between time, treadmill speed, slope and stress index S for a subject running on a treadmill is shown in Table 1.

TABLE 1

| Exercise Time Minutes | Treadmill Speed Miles/Hour | Slope of Treadmill % | Stress Index S |
|---|---|---|---|
| 1 | 2.0 | 4 | 0.85 |
| 3 | 2.5 | 8 | 0.86 |
| 6 | 2.5 | 12 | 1.00 |
| 9 | 3.0 | 14 | 1.14 |
| 12 | 3.5 | 14 | 1.36 |
| 15 | 3.5 | 16 | 1.55 |
| 18 | 3.5 | 18 | 2.00 |
| 21 | 4.0 | 18 | 3.20 |
| 24 | 4.0 | 20 | |

The subject ran on the treadmill for 1 minute at a speed of 2 miles per hour with the treadmill at 4% slope. Thereafter the subject ran 2 minutes (total elapsed time 3 minutes) at 2.5 miles per hour and 8% slope. Thereafter the subject ran three miles per hour (total elapsed time 6 minutes) at 2.5 miles per hour and 12% slope. The exercise terminated after 24 minutes during which the last three minutes of exercise was carried out at 4 miles per hour on a treadmill having a slope of 20%.

After termination of the exercise at $t_4$, the stress index descends, indicating recovery from the exercise stress. At time $t_5$ where the stress index S equals 2, the metabolism reverts from anaerobic to aerobic, meaning that the subject remained in the anaerobic region during the time period $t_4$ to $t_5$. At the time $t_6$ where the stress index equals 1, complete recovery from the exercise stress has occurred. It is desirable to shorten the time period $t_4$ to $t_6$ by a procedure called warm-down. Monitor 16 permits the design and quantitative control of the warm-down procedures.

Some subjects, such as sprinters, require muscle exercise at high speeds corresponding to large work loads of short duration which intentionally convert their metabolism to anaerobic. These subjects typically sprint a short distance and then recover by running at a slower speed. This procedure is called interval training for which at this time, no objective guide instruments exist. Monitor 16 permits the correct design and quantitative control of this interval training, commencing sprints at such times when the stress meter indicates preselected values such as 1 (complete stress recovery) or 2 (partial recovery from the anaerobic metabolism) and terminating sprints when the stress index has reached another preselect anaerobic value.

Some athletic events such as soccer, basketball, gymnastics, etc., require certain skills. If these skills are performed improperly, a stress is placed upon the subject's system because too much energy is expended, causing the stress index S to rise. The stress meter permits identification of these errors by indicating a temporary rise of the stress index. Further, a video camera and video recorder system (not shown) may be correlated with the stress meter at output jack 9 (FIG. 4) to provide a record of the exercising athlete's technical errors. By comparing the instantaneous stress index values during the exercise with the video recordings, the interrelation of biomechanics and physiology is made visible to the exercising subject, thereby providing the subject with objective means for improvement.

1.2 Exercise Machines and Weight Lifting

Figure 7:
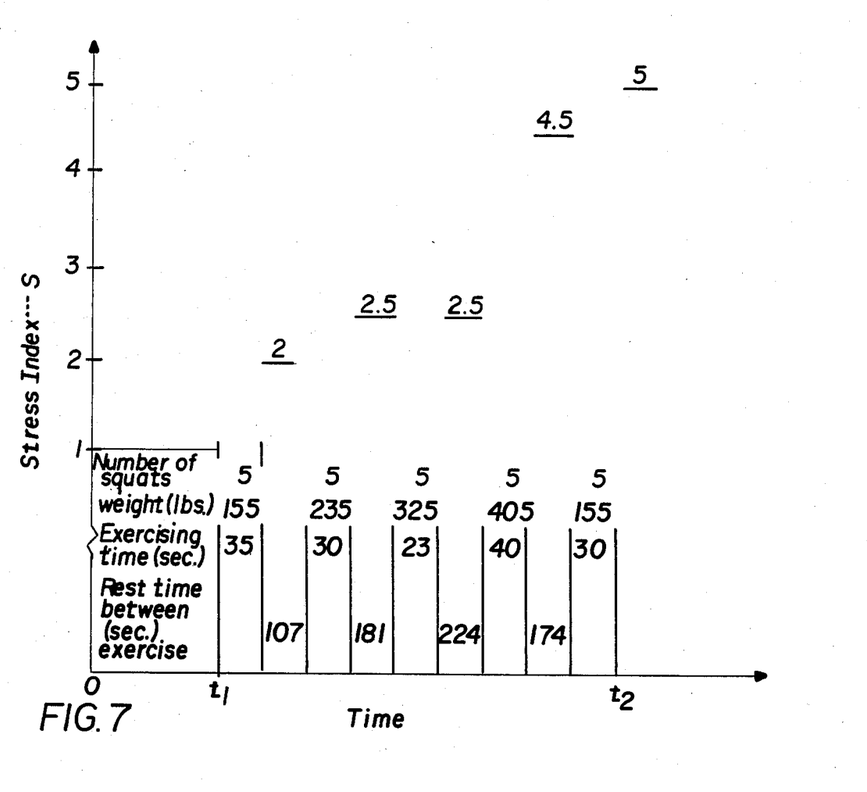
FIG. 7 is a graphical representation of the change of the stress index S during a set of exercises on an exercising machine.

The stress index S presents a similar behavior during and after weight lifting or working out on an exercise machine as was shown for running in FIG. 6. Subjects lifting weights or working out on exercise machines are engaged in repetitions of a specific exercise. FIG. 7 shows the change of stress index plotted versus time for a subject engaged in a repetitive set of squats. Number of squats, weight lifted, exercising time and rest time between exercises are listed on the bottom of FIG. 7. The exercising regimen was designed by the subject. The stress meter was used to evaluate the subject's work-out. The first squat set of 155 lbs. was designed by the subject as a warm-up. The stress meter measures a stress index of 2 indicating that a useful warm-up period had been exceeded and that a work-out had commenced. The second and third set of squats at 235 lbs. and 325 lbs. respectively produced a stress index S of 2.5 which indicates that the subject was slightly anaerobic prior to the intended maximum weight squats. At least one of the two sets should have been omitted.

The next squat set with maximum weight produced a stress index S of 4.5. Through experiments with world class athletes it has been established that these athletes can reach stress index values of 10. FIG. 7 thus suggests that the subject could have selected a higher weight. The last set of squats at 155 lbs. was done by the subject to warm-down his system. Contrary to the subject's intention, the stress index S reached a value of 5, indicating that further unwanted stress had been imposed upon the subject's body.

This example demonstrates the difficulties involved in weight lifting and explains the high rate of injuries and failure to improve.

The stress meter with its monitor 16 permits the correct design and quantitative control of number of squats, weight, exercising time and resting time between sets.

Subjects engaged in an exercising regimen, such as jogging or working out on exercising machines solely for the purpose of maintaining their cardiopulmonary health, and subjects engaged in a cardiopulmonary rehabilitation program need not work out in the anaerobic region. Exercising subjects may use a heart rate monitor while the rehabilitation subjects are customarily monitored as to their ST segments. The stress meter permits, via monitor 16, the correct design and quantitative control of the work load thus assuring safety of their program by indicating an alarm when a stress index S of 2 is reached.

Fitness Index

A fitness index F can be defined as the amount of work measured in kpm (kilopond meters) or METs (Multiple of resting Energy Requirement) to be expended to raise the stress index S to a value of 2. If progress has been made by a subject engaged in a health maintenance program or in a rehabilitation program, it is indicated by the fact that the amount of work necessary to raise the stress index to 2 increases. Means are provided to interconnect the stress meter with an ergometer to measure the fitness index F to monitor success of a rehabilitation and maintenance program.

Figure 8:
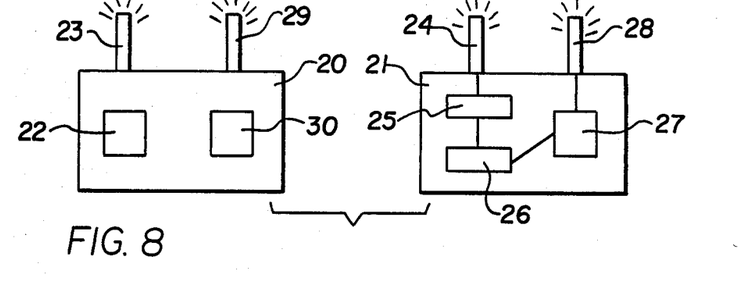
FIG. 8 is a schematic illustration of the present invention in a telecommunication mode with a portable sensing unit and remote analysis unit.

FIG. 8 illustrates a remote exercise control system wherein a sensing device 20 is carried by the subject and a remote analysis unit 21 is maintained in telecommunication contact with the sensing device 20 through transmitting antennas 23, 28 respectively and receiving antenna 29, 24 respectively. The sensing device 20 as carried by the subject is connected through communication means to the remote analysis unit 21. The sensing device 20 includes a discriminator 22 which delivers an appropriate electrical transmission signal through the antenna 23 indicating instantaneous EKG data for the subject. At the remote analysis unit 21 the receiving antenna 24 receives the signal from the sending antenna 23 and manipulates the data through appropriate discriminator and comparator devices 25 and an appropriate memory device 26. The remote analysis unit 21 also includes a signal generator 27 which delivers a communication signal through the transmitting antenna 28 based upon the instantaneous value of the subject's Stress Index S. The communication signal from the antenna 28 is received by the subject's sensing device 20 to a receiving antenna 29 which delivers the signal to an appropriate indicator device 30 such as an audible or visible signal generator or a display device.

By employing the system of FIG. 8, an individual athlete may carry with him the lightweight sensing device 20 and may be guided in his exercise workout through telecommunications from a remote analysis unit 21. The remote analysis unit 21 may be appropriately multiplexed to service multiple athletes concurrently.

Figure 9:
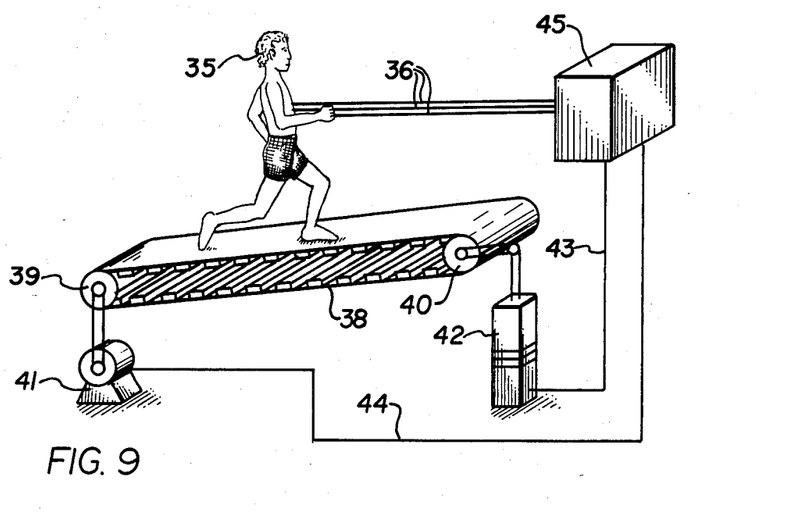
FIGS. 9 and 10 are schematic illustrations of embodiments of the invention when an exercise device is regulated by means of a stress index S measurement.

In FIG. 9, a subject identified by the numeral 35 has a training workout controlled by means of instantaneous measurements of the stress index S. The subject 35 has appropriate electrical connections 36 to an electromechanical device 45 of the type as an EKG 4A and a stress index meter 4B illustrated in FIG. 3.

As shown in FIG. 9, the subject 35 is exercising on a treadmill 38 connected between parallel rollers 39, 40. An electrical motor 41 drives one of the rollers 39. A hydraulic cylinder 42 is connected to the axle of the other roller 40 to regulate the elevation of the axle of the roller 40 and thereby alter the difficulty of the treadmill.

As the stress index S of the subject 35 is determined in the electromechanical device 4b, the stress index S value with respect to time can be maintained by regulating the speed of the treadmill by means of a signal through a conductor 44 which alters the speed of the motor 41 and/or by regulating the elevation of the roller 40 by means of a signal through a conductor 43 to activate the hydraulic cylinder 42 upwardly or downwardly.

By employing the system of FIG. 9, the exercising workout of the subject 35 can be optimized to maintain a desired slope for the stress index S versus time characteristic.

Figure 10:
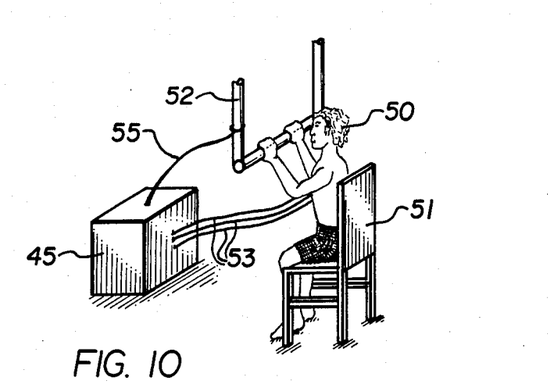

In FIG. 10 a further embodiment of the invention is illustrated wherein a subject 50 is seated or supported by a chair or frame 51 and is provided with a mechanical exercise device 52 to be pushed, pulled, turned or otherwise moved against controllable resistance. Such exercising devices are known in the athletic training art, for example, Nautilus machines. The subject 50 has appropriate wiring connections 53 to an appropriate electromechanical device 54 which controls the resistance of the exercise machine 52 through an electrical conductor 55. The arrangement may be such that the subject 50 is compelled to maintain a pre-selected slope of the stress index S versus time characteristic as described in connection with FIG. 9. Alternatively, the resistance of the exercise device 52 may be reduced when the stress index S of the subject 50 reaches a value of 2.0 or some other value corresponding to the aerobic-/anaerobic threshold.

2. Cardiopulmonary Vital Capacity

As shown in FIG. 4, the stress number Z changes from heartbeat-to-heartbeat during normal breathing, that is, inhalation and exhalation of air. A drastic change in the stress number Z occurs during deep inhalation of air. The relationship of the stress index S with deep inhalation is called cardiopulmonary vital capacity.

When measuring cardiopulmonary vital capacity, the lowest value of the stress number Z (after inhalation) is compared with the value of the stress number Z (before stress).

Figure 11:
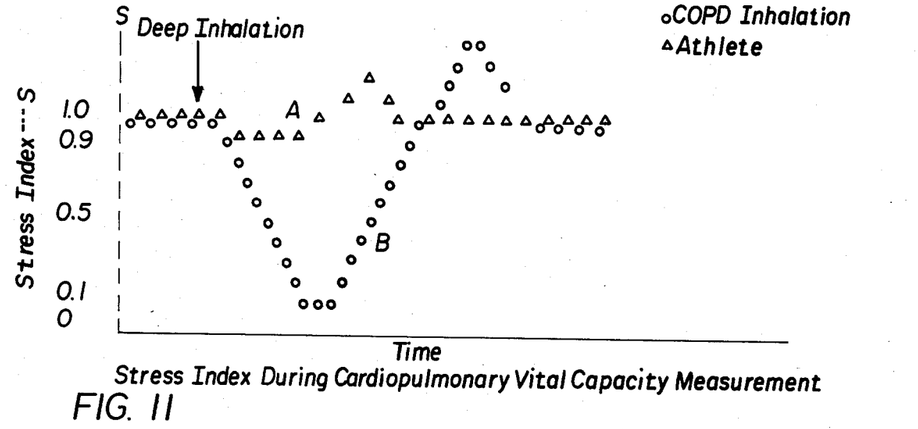
FIG. 11 is a graphical representation of the stress index S during a cardiopulmonary vital capacity measurement.

When performing a cardiopulmonary vital capacity measurement the body becomes oxygenated during the inhalation phase thus representing a relief of stress which is indicated by a decrease of the stress index S. During the exhalation phase the body lacks oxygen thus representing the application of a stress which is indicated by an increase of the stress index S. The decrease of the stress index S during the inhalation phase ranges from 0.9 for COPD (Chronic Obstructive Pulmonary Disease) patients to 0.1 for athletes in excellent training condition comprising the two extreme cases. This relationship is shown in FIG. 11. Normal persons not engaged in physical activity display stress index values between 0.6 and 0.1 during a cardiopulmonary vital capacity test. Subjects who cannot reduce their stress index below 0.6 should consider undertaking a rehabilitation therapy.

Table 2 lists the Stress Index S during a cardiopulmonary vital capacity measurement prior to and after a rehabilitation therapy.

TABLE 2

| Subject | Decrease in Stress Index Before Therapy | Decrease in Stress Index After Therapy |
|---|---|---|
| 1 | 0.9 | 0.65 |
| 2 | 0.85 | 0.55 |
| 3 | 0.92 | 0.58 |
| 4 | 0.71 | 0.43 |
| 5 | 0.68 | 0.35 |

Table 2 suggests that cardiopulmonary vital capacity measurements are suitable to judge and demonstrate the success of a rehabilitation therapy. They also can be used to maintain cardiopulmonary health by providing simple instrumentation whereby a subject can hold two EKG electrodes connected to a stress meter and take a deep breath every morning to obtain a quantitative reading on the present cardiopulmonary health.

The stress index S, being a quick, non-invasive, non-expensive, easy and practical measurement, can thus become the standard throughout the world for cardiopulmonary health assessment and maintenance. Its value should be routinely measured whenever a physician treats a patient and should be stored in medical records and on medical emergency cards.

3. Oxygen Inhalation

Concentration and flow rate of oxygen inhalation for a medical patient is currently selected in the following manner: The patient's arterial blood gases are initially determined. On the basis of these results, and the general condition of the patient, age, weight, etc., the physician derives subjectively and empirically an appropriate concentration and flow rate taking prior experience into account. Progress or regress is monitored further by using transcutaneous oxygen meters which indicate only a trend but no absolute values. Alternative arterial blood gas sampling can be a painful procedure.

If oxygen inhalation is indicated in a cardiopulmonary stress situation it will relieve the stress which is objectively measured by a decrease of the stress index S. Oxygen, when inhaled in too large concentrations and/or too high flow rates, may also become stressfully toxic in which case the stress index S increases. The stress index S therefore becomes the first objective measure to quantitatively select beneficial concentrations and flow rates for oxygen inhalations.

Figure 12:
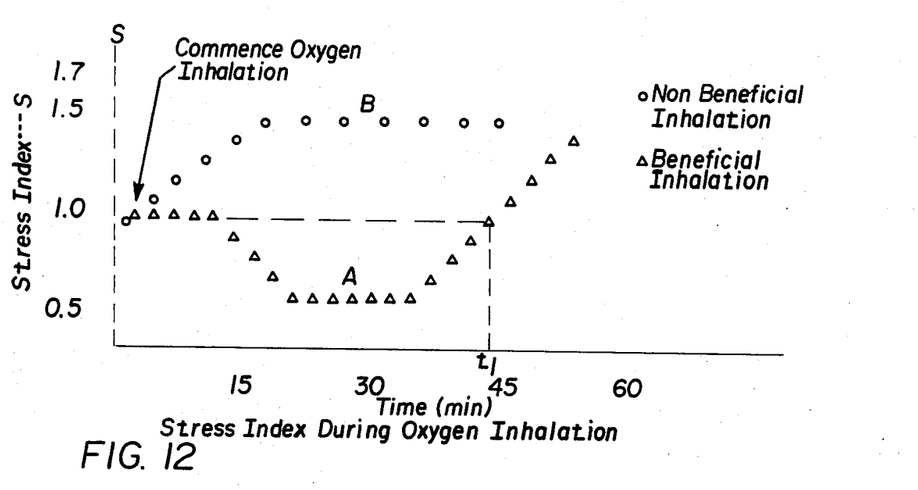
FIG. 12 is a graphical representation of the stress index S during oxygen inhalation.

As show in in FIG. 12, curve A, during a beneficial oxygen inhalation, the stress index S decreases initially (beneficial phase to relieve stress), then reaches a plateau (minimum) and at a later time increases again (non-beneficial toxic phase—application of stress). The stress index S thus is an indicator for the length of time an oxygen inhalation should be administered. In the case of the subject of curve A, FIG. 12, the oxygen inhalation should terminate at 45 minutes, when the stress index S restores to 1.0. FIG. 12, curve B shows a non-beneficial oxygen inhalation, i.e., the stress index S immediately increases above 1.0. It is important to note that neither arterial blood gas measurements nor transcutaneous measurements are capable to detect the plateau at which oxygen inhalation becomes non-beneficial and eventually toxic. Both prior techniques do not monitor efficacy and safety. However, the S-Index technique does indicate such transitions instantaneously.

On the cardiopulmonary stress scale beneficial oxygen inhalations develop a stress index S in the range between 0.6 and 1.0, while non-beneficial oxygen inhalations are indicated by stress index S between 1.0 and 2.0.

Machinery can be constructed which is controlled by the readings of the stress meter and which automatically change concentration and/or flow rate during oxygen inhalation such that an oxygen inhalation is always beneficial. This machinery may also sound alarms in cases when oxygen inhalation becomes stressful or toxic.

Other machinery can also be constructed which is controlled by the readings of a stress meter and which monitors continuously the cardiopulmonary health status of patients in an intensive care unit or during and after surgery, or during and after application of anaesthesia.

Other machinery can be developed which is controlled by the readings of a stress meter and which monitors continuously the cardiopulmonary health status of pacemaker-wearing patients to turn on or off pacemakers upon demand.

The stress index S permits automatic monitoring of all oxygen inhalation therapies to assure efficacy and safety.

4. Cardiac Stimulants

Figure 13:
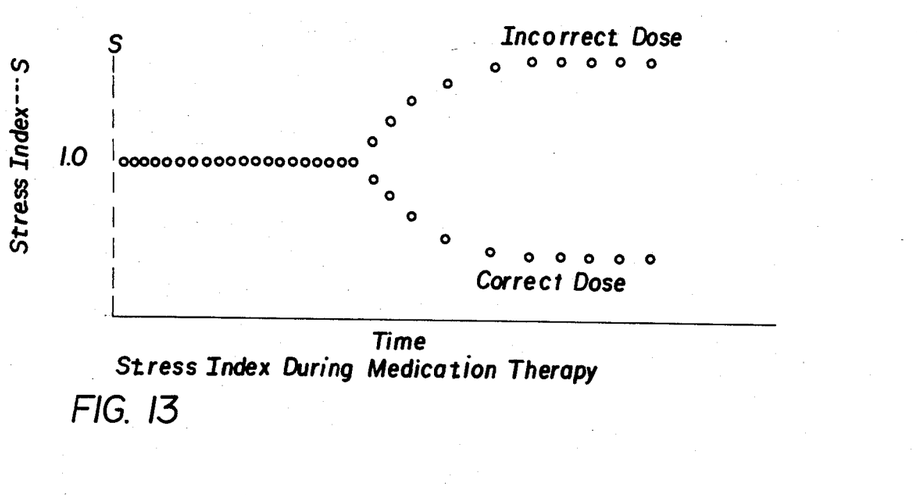
FIG. 13 is a graphical representation of the stress index S during medication therapy.

The efficacy of medication especially cardiac medication can be measured by the stress index S which decreases for correct doses (relief of stress) and increases for incorrect doses (application of stress) as shown in FIG. 13.

5. Cardiopulmonary Rehabilitation and Maintenance Therapies

The utility and significance of this invention can be illustrated by the discovery of new techniques to improve and effectively maintain cardiopulmonary health. The efficacy and safety of these techniques is controlled by the stress meter.

It is established procedure to judge cardiopulmonary fitness by the maximum oxygen consumption. The higher it is, the better is the fitness. There exist statistical data that the probability of suffering a heart attack is directly related to the maximum oxygen consumption of a subject. It is therefore a goal of rehabilitation therapy to improve the maximum oxygen consumption and goal of many health maintenance programs to maintain as high an oxygen consumption as possible. Many of these improvement and maintenance programs contain some sort of exercise which as previously pointed out is difficult to measure with conventional devices.

Figure 14:
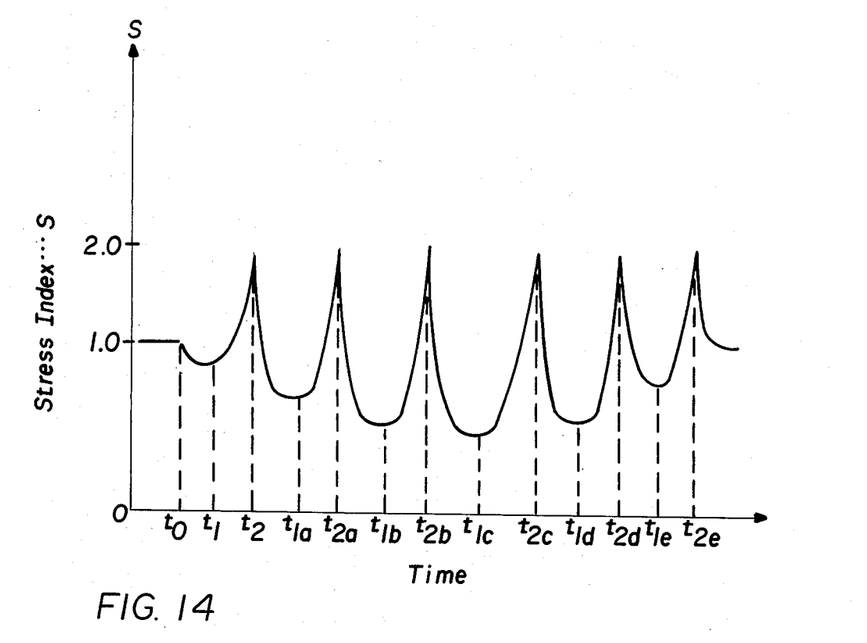
FIG. 14 is a graphical representation of the stress index S during a cardiopulmonary rehabilitation and maintenance therapy.

A new technique to improve and maintain cardiopulmonary health employs the stress meter and is based upon beneficial oxygen inhalations and subsequent utilization of excess oxygen by engaging in exercise. Both components are precisely controlled by the stress meter. FIG. 14 shows the procedure just explained. After establishing a "rest" stress index of 1 a time $t_0$, oxygen-enriched air is inhaled. When the subject's system is loaded with oxygen which occurs when the stress index displays a minimum at time $t_1$, thus indicating no further benefit could be obtained from continued oxygen inhalation, an exercising regimen commences for the purpose of consuming and utilizing the excess oxygen. The exercising regimen is continued until time $t_2$, when the stress index S becomes 2, i.e., the anaerobic threshold is reached and exercise is terminated. It is then observed that the stress index S declines to a new low at time $t_{1a}$ when a second exercise regimen commences and continues until the stress index S reaches a value of 2.0 at time $t_{2a}$, indicating the anaerobic threshold. This procedure of alternative oxygen loading and subsequent withdrawal in incremental steps has led to very impressive results hitherto unknown. It should be pointed out that this new technique is not restricted to treatment of medical patients but works for all subjects independent of their present health status.

Figure 15:
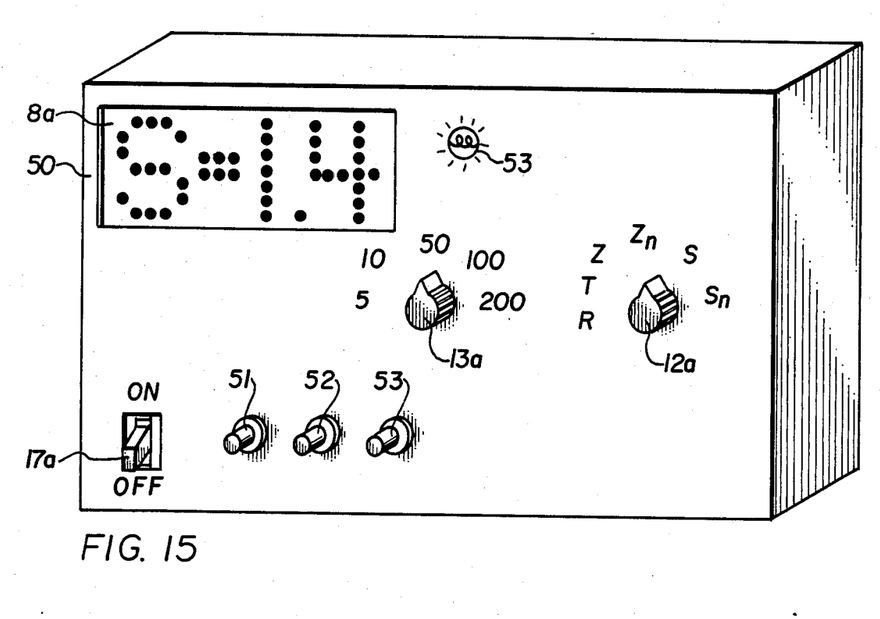
FIG. 15 is a sketch of a preferred embodiment of the stress meter of this invention.

A particularly preferred embodiment of the stress index device is illustrated in FIG. 15 wherein a casing 50 includes a digital display unit 8a, an on/off switch 17a, a mode selection switch 12a, a sliding average selection switch 13a, a start button 50, a reset button 51, an "accept" button 52 and a lamp 53. The sliding average switch 13a permits selection of the number of heartbeats to be employed by the operator in determining a sliding average of the observed values. By employing a sliding average, the heartbeat-to-heartbeat fluctuations can be dampened and a meaningful value can be obtained. The digital display unit 8a can be adjusted by the mode selection switch 12a to display a variety of functions including:

R—the peak amplitude of the R wave
T—the peak amplitude of the T wave
Z—the instantaneous R/T ratio
$Z_n$—the instantaneous sliding average of the R/T ratio
S—the instantaneous stress index
$S_n$—the stress index based upon a sliding average.

The function of the start button 50 is to permit the digital display unit 8a to display the value $Z_n$. After the value of $Z_n$ has leveled to an essentially unchanging value (e.g. 4.5, 4.55, 4.5 etc.) over a number of time-spaced displays, the operator can accept the displayed value of $Z_n$ as the starting value, i.e., $Z_{Before}$. The operator then activates the accept switch 52 to record the value of $Z_{Before}$ in the memory device of the stress index meter. The meter then enters into the operating mode and provides a digital display for every heartbeat or for every selected number of heartbeats or for every selected increment of time.

The lamp 53 normally is set to blink once for every heartbeat.

Thus the stress meter of FIG. 15 is simple to operate and provides instantaneous indications of the cardiopulmonary condition of a subject as herein described.

It should be observed that the stress index as defined in this patent specification is the instantaneous ratio of $Z_{After}/Z_{Before}$, when the values of Z are obtained as the ratio of the amplitude of the peak R wave to the amplitude of the peak T wave. These relationships provide S values ranging from zero to 10 and present a 1.0 value when the subject is at rest without application of stress or without relief of stress. It should be apparent that the inversion of the Z value can be adopted, i.e., the ratio of the T-wave peak to the R-wave peak can be calculated as a "before" condition and as a "after" condition. The ratios of the inverted ratios can be employed to develop a counterpart of the stress index which is herein described without departing from the spirit and scope of the present invention.

EXAMPLE $$Z_B = Z_{Before} = T_1/R_1$$

$$Z_A = Z_{After} = R_2/T_2$$

$$S = \frac{Z_A}{Z_B} = \frac{R_2/T_2}{R_1/T_1} = \frac{R_2 T_1}{R_1 T_2}$$

The range of S is 0 to 10 and the practical range is about 0.2 to 5.

The function can be inverted, thus $$\frac{1}{S} = \frac{T_1 R_2}{T_2 R_1}$$

when the practical value of 1/S is about 5 to about 2.

However it should be re-emphasized that the stress index, as specifically illustrated and described herein, is preferred because of the convenience of understanding and interpretation when the observable range is from zero to 10.

I claim:

1. An electromechanical device to indicate cardiopulmonary stress condition of a subject comprising:

means for developing the EKG wave of the subject including electrical sensors suitably positioned on the subject to establish the EKG wave with a well defined R and T wave;

means for determining and recording the ratio of the R-peak to the T-peak while the subject is at rest to establish a stress value Z(before);

means for determining and recording the ratio of the R-peak to the T-peak as the subject is subjected to stress or to relief of stress to establish the stress Z(after);

means for establishing Stress Index S as $$\frac{Z(after)}{Z(before)}$$

and means for indicating the value of the Stress Index S.

2. The electromechanical device of claim 1 including means for establishing a sliding average value of the stress value Z, determined over a preselected number of heartbeats.

3. The electromechanical device of claim 1 including means for establishing a sliding average value of the stress value Z, determined over a preselected time interval.

4. The electromechanical device of claim 1 including electronic memory circuitry and means for storing the value of Z(before) and the Stress Index values for a particular subject.

5. The electromechanical device of claim 1 including an indicator means for emitting an identifiable signal when the value of the Stress Index S exceeds a pre-established value.

6. The electromechanical device as defined in claim 1 including indicating means to identify a minimum value of the Stress Index immediately following initiation of an exercise program.

7. The electromechanical device as defined in claim 1 including signal generating means to indicate the return of the Stress Index following exercise to levels prior to exercise program.

8. The electromechanical device of claim 1 including work measuring means for measuring the amount of work carried on by the subject to achieve a preselected level of the Stress Index.

9. The electromechanical device of claim 8 including memory means for recording the work value of each work program and further including means for comparing the amount of work for successive exercise programs required to achieve the predetermined value of the Stress Index.

10. The electromechanical device of claim 1 including telecommunication means for delivering an electrical signal corresponding to the said R-peak and T-peak to a remote location for analysis.

11. The electromechanical device of claim 10 including means for delivering a signal from said remote location back to the exercising subject to indicate the Stress Index.

12. The electromechanical device of claim 1 in combination with an exercising machine; including regulating means for increasing or decreasing the resistance of the machine to exercising activity; means responsive to the instantaneous value of the Stress Index of said subject for altering said regulating means and thereby increasing or decreasing the resistance of said exercise machine.

13. A method of determining the stress condition of a subject which comprises:
   determining the Stress Index of the subject at rest by establishing as Z(before) the ratio of the subject's electrocardiograph wave R-peak to the T-peak; thereafter subjecting the subject to stress; and, thereafter measuring the stress value Z following stress application as Z(after);
   thereafter determining the ratio Z(after)/Z(before) as the Stress Index S.

14. The method of conducting physical exercise which comprises determining the stress value Z for the exercising subject prior to exercise by dividing the subject's electrocardiograph wave R-peak value by the T-peak value to determine Z(before);
   thereafter carrying out a physical exercise activity;
   periodically or continuously measuring the stress value Z of the exercising subject as Z(after) and continuing the exercise activity until the ratio Z(before)/Z(after) is in the range 1.0 to 2.0.

15. An electromechanical device comprising:
   electrode means for observing the instantaneous EKG wave of a subject as an input electrical signal including a repeating wave pattern having an R-peak and a T-peak;
   means for delivering said electrical signal to an electrical circuit including
   means for determining the amplitude of said R-peak and said T-peak;
   means for determining the ratio of the amplitude of said R-peak to the amplitude of said T-peak, said ratio being identified as Z;
   means for determining the ratio of selected values of Z to other selected values of Z to develop a ratio signal S;
   means for storing selected values of Z and S;
   means for indicating the instantaneous value of a function related to the value S.

16. The device of claim 15 wherein said electrode means includes three distinct electrodes arranged to deliver a electrocardiograph wave including well delineated R- and T-peaks.

17. The device of claim 15 including means for inverting the value of Stress Index S and including readout means for indicating the instantaneous value of the inverted Stress Index S.

18. The method of determining the cardiopulmonary vital capacity of a subject which comprises:
   establishing an initial Stress Index S for the subject by determining while the subject is not experiencing a stress, the ratio of the amplitude of the subject's EKG "R-peak" to the amplitude of the subject's EKG "T-peak", said ratio identified as Z(before); and determining thereafter the ratio of the amplitude of the subject's EKG "R-peak" to the amplitude of the subject's EKG "T-peak", said ratio identified as Z(after); establishing a Stress Index for the subject as the ratio of Z(after) to Z(before);
   continuously observing the Stress Index of the subject while the subject experiences a single deep inhalation;
   observing the minimum Stress Index value of the subject immediately following the said deep inhalation as an indicstion of the said cardiopulmonary vital capacity.

19. A method for monitoring oxygen inhalation therapy of a subject which comprises:
   establishing the initial Stress value for the subject by determining while the subject is not experiencing a stress, the ratio of the amplitude of the subject's EKG "R-peak" to the amplitude of the subject's EKG "T-peak", said ratio identified as Z(before) whereby the initial Stress Index has a value of 1.0;
   providing oxygen-rich air to the subject for inhalation;
   continuously observing the Stress Index of the subject while the subject is inhaling oxygen rich air by determining thereafter the ratio of the amplitude of the subject's EKG "R-peak" to the amplitude of the subject's EKG "T-peak", said ratio identified as Z(after); establishing a Stress Index for the subject as the ratio of Z(after) to Z(before);
   maintaining the concentration of oxygen in the oxygen rich air at a sufficient level to cause the said Stress Index of the subject to decrease from an initial Stress Index=1.0 and thereafter to rise above the said initial Stress Index;
   terminating the oxygen inhalation therapy after the Stress Index of the subject exceeds 1.0 and before the Stress Index of the subject reaches 2.0.

20. An oxykinetic therapy treatment for a subject comprising:
   establishing an initial Stress value for said subject immediately prior to the treatment by determining while the subject is not experiencing a stress, the ratio of the amplitude of the subject's EKG "R-peak" to the amplitude of the subject's EKG "T-peak", said ratio identified as Z(before);
   supplying oxygen enriched air for the subject to breath until the Stress Index of the subject reaches a minimum level; thereafter exercising the subject to utilize excess oxygen; determining thereafter the ratio of the amplitude of the subject's EKG "R-peak" to the amplitude of the subject's EKG "T-peak", said ratio identified as Z(after); establishing a Stress Index for the subject as the ratio of Z(after) to Z(before); and continuing the exercise until the Stress Index exceeds a value of 1.0 and discontinuing the exercise before the Stress Index reaches a value of 2.0;
   continuing to supply oxygen enriched air to the non-exercising subject while the subject's Stress Index falls.

21. The oxykinetic therapy of claim 20 wherein the subject breaths oxygen enriched air throughout the entire oxykinetic therapy treatment.

22. The oxykinetic therapy treatment of claim 20 wherein the exercise is repeated by the subject after a period of non-exercise during which the subject's Stress Index falls and continuing the exercise until the Stress Index again increases and discontinuing the exercise before the Stress Index rises to a value of 2.0; and continuing to supply oxygen enriched air to the subject throughout the entire oxykinetic therapy treatment.

* * * * *